(12) United States Patent
Fehr et al.

(10) Patent No.: US 8,961,872 B2
(45) Date of Patent: Feb. 24, 2015

(54) USE OF A STERILIZATION AGENT FOR ENHANCING HEMOCOMPATIBILITY

(75) Inventors: Thorsten Fehr, Losheim am See (DE); Claus Haupert, Nalbach, DE (US); Franz Kugelmann, St. Wendel (DE); Nicole Simon, Schmelz (DE); Ansgar Erlenkoetter, St. Wendel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 105 days.

(21) Appl. No.: 13/808,459

(22) PCT Filed: Jul. 5, 2011

(86) PCT No.: PCT/EP2011/003331
§ 371 (c)(1),
(2), (4) Date: Mar. 25, 2013

(87) PCT Pub. No.: WO2012/003962
PCT Pub. Date: Jan. 12, 2012

(65) Prior Publication Data
US 2013/0195716 A1    Aug. 1, 2013

(30) Foreign Application Priority Data
Jul. 5, 2010    (DE) .......................... 10 2010 026 104

(51) Int. Cl.
*A61L 9/00* (2006.01)
*A61L 2/18* (2006.01)
*A61L 2/20* (2006.01)
*F16L 11/00* (2006.01)
*A61L 2/08* (2006.01)
*A61L 2/10* (2006.01)

(52) U.S. Cl.
CPC ................. *A61L 2/186* (2013.01); *A61L 2/202* (2013.01); *A61L 2/208* (2013.01); *F16L 11/00* (2013.01); *A61L 2/081* (2013.01); *A61L 2/10* (2013.01); *A61L 2202/122* (2013.01); *A61L 2202/14* (2013.01); *A61L 2202/24* (2013.01)
USPC ....................... 422/28; 422/1; 422/29; 422/32

(58) Field of Classification Search
CPC ............ A61L 2/00; A61L 2/208; B05D 1/00; B08B 3/00; C12H 1/00
USPC ............ 422/1, 28–29, 32, 261, 292; 134/6, 8, 134/14, 22.11; 424/76.8; 252/380, 186.1
See application file for complete search history.

(56) References Cited

FOREIGN PATENT DOCUMENTS

| DE | 29916454 | 12/1999 | |
|---|---|---|---|
| EP | 1829558 | 9/2007 | |
| WO | WO-97/19594 | 6/1997 | |
| WO | WO-03/076089 | 9/2003 | |
| WO | WO 03/076089 A1 * | 9/2003 | ................ B08B 9/00 |

OTHER PUBLICATIONS

International Search Report for PCT/EP2011/003331 mailed Sep. 30, 2011 (published as WO 2012/003962) (2 pages).

* cited by examiner

*Primary Examiner* — Monzer R Chorbaji
(74) *Attorney, Agent, or Firm* — Choate, Hall & Stewart LLP (57) ABSTRACT

The invention concerns the use of a sterilization agent comprising $H_2O_2$ or a derivative thereof, capable of generating $H_2O_2$ as the sterilising component under sterilization conditions, for enhancing the hemocompatibility of objects.

13 Claims, 7 Drawing Sheets

USE OF A STERILIZATION AGENT FOR ENHANCING HEMOCOMPATIBILITY

BACKGROUND OF THE INVENTION

The invention relates to the use of a sterilization agent comprising $H_2O_2$ (hydrogen peroxide) or a derivative thereof.

Sterilization in the context of the present invention means any process that eliminates or kills all forms of life, including transmissible agents, such as fungi, bacteria, viruses, spore forms, etc. present on a surface, contained in a fluid, in medication or in a compound such as biological culture media. Sterilization methods include applying the proper combinations of heat, chemical agents, irradiation (gamma rays, e-beam, etc.), high pressure and/or filtration.

Sterilization of objects, in particular object used in medicine, such as objects that have contact with blood during use is known since long. Commonly used sterilization procedures use ETO or other chemicals such as ozone or hydrogen peroxide, gamma radiation, steam, or combinations thereof. In this regard, reference is made to EP 1 175 230 and EP 1 455 843 and the prior art cited therein.

In many medicinal operations, e.g. surgeries and extracorporeal blood circulation applications, such as in hemodialysis, wherein wastes and water are removed by circulating blood outside the body through an external filter, called a dialyzer, that contains a semipermeable membrane, the sterility of the objects in contact with blood is extremely important.

This is because patients who have to undergo a treatment including extracorporeal blood circulation, especially hemodialysis patients with nearly daily treatment, suffer a strong risk of inflammation which can in the worst case end in a sepsis.

In extracorporeal blood circulation applications, it is furthermore important that the blood does not coagulate or the quality of the blood is deteriorated while the blood is outside of the body. Due to this, it would be advantageous to dispose over a sterilizer which eases the transport and the storage of blood in extracorporeal blood circulation applications.

Any of the above mentioned sterilization methods has an impact on the surface properties of the sterilized object. In the case of chemical agents, these can as well penetrate into the surface of the object and remain there, if the same has a porous structure.

Some of the sterilization methods have a reduced compatibility with certain materials. For example, gamma radiation has a degrading effect on the surface of polypropylene objects. Yet, for other materials, a certain sterilization method may have a positive or negative effect on the surface in view of certain applications.

Therefore, it is an object of the present invention to provide a sterilization agent, in particular for extracorporeal blood circulation applications that assures a safe and reliable sterilization and influences the surface of objects in a positive manner for the contact with blood while being easily and economically to implement in a sterilization process.

SUMMARY OF THE INVENTION

This object is achieved by the teaching according to claim 1. Preferred embodiments are claimed in the dependent claims.

In one embodiment the invention relates to the use of a sterilization agent comprising $H_2O_2$ or a derivative thereof, capable of generating $H_2O_2$ as the sterilising component under sterilization conditions, for enhancing the hemocompatibility of objects.

In one embodiment the invention relates to the use of a sterilization agent, wherein the object is a medical object, in particular an object that may be in contact with blood during use.

In one embodiment the invention relates to the use of a sterilization agent, wherein the object is a medical object useful in hemodialysis.

In one embodiment the invention relates to the use of a sterilization agent, wherein the object is a tubing system.

In one embodiment the invention relates to the use of a sterilization agent, wherein the sterilzation agent comprising $H_2O_2$ or a derivative thereof, capable of generating $H_2O_2$ as the sterilising component under sterilization conditions is used in combination with other sterilization means or agents.

In one embodiment the invention relates to the use of a sterilization agent, wherein said sterilization means or agent is selected among one or more of heat, UV or gamma radiation, or chemical or biological sterilization components, in particular ozone.

In one embodiment the invention relates to the use of a sterilization agent, which comprises $H_2O_2$ or a derivative thereof, capable of generating $H_2O_2$ as the sterilising component under sterilization conditions, or a mixture of two or more thereof, as the only sterilising component.

In one embodiment the invention relates to the use of a sterilization agent, wherein $H_2O_2$ under sterilization conditions has a concentration of 3% w/w to 90% w/w, preferably 10% w/w to 90% w/w, more preferably 30% w/w to 90% w/w, even more preferably 30% w/w to 60% w/w and most preferably 30% w/w to 40% w/w.

In one embodiment the invention relates to the use of a sterilzation agent, wherein said derivative is selected among peracids, carbamide peroxides, triphenyiphosphine oxide and acetone peroxide.

In one embodiment the invention relates to the use of a sterilization agent, wherein the enhanced hemocompatibility comprises at least one of the following characteristics: reduction of the level of coagulation activation, a reduction of the loss of platelets, a lower concentration of anaphylatoxin C5a, and a decrease in hemolysis during use of the object.

In one embodiment the invention relates to the use of a sterilization agent comprising $H_2O_2$ or a derivative thereof, capable of generating $H_2O_2$ as the sterilising component under sterilization conditions for achieving at least one of the following characteristics within an object: reduction of the level of coagulation activation, a reduction of the loss of platelets, a lower concentration of anaphylatoxin C5a, and a decrease in hemolysis, respectively during use of said object, e.g. during contact with blood of said object.

In one embodiment the invention relates to the use of a sterilization agent, wherein the enhancement of hemocompatibility, the reduction of the level of coagulation activation, the reduction of the loss of platelets, the lower concentration of anaphylatoxin C5a, and the decrease in hemolysis during use of said object, e.g. during contact with blood of said object, are respectively achieved compared to an object that has been sterilized with a sterilization agent not containing $H_2O_2$.

DETAILED DESCRIPTION OF THE INVENTION

According to the invention, a sterilization agent comprising $H_2O_2$ or a derivative thereof, capable of generating $H_2O_2$ under sterilization conditions, is used for enhancing the hemocompatibility of objects.

$H_2O_2$ (hydrogen peroxide) is a chemical sterilization agent. It is a strong oxidant destroying a wide range of pathogens and it is used to sterilize heat or temperature sensitive objects such as rigid endoscopes. In medical sterilization $H_2O_2$ is used at relatively high concentrations, ranging from around 0% w/w up to 90% w/w. The biggest advantage of $H_2O_2$ as a sterilizer is the short cycle time. Whereas the cycle time for ethylene oxide (ETO), another chemical sterilization agent, may be 10 to 15 hours, the use of high concentrations of $H_2O_2$ allows much shorter cycle times.

Depending on what kind of object is being sterilized, different concentrations of $H_2O_2$ are advantageous, particularly to avoid degradation of the object to be sterilized.

In a further embodiment of the invention, $H_2O_2$ under sterilization conditions has a concentration of 30% w/w to 90% w/w, preferably 10% w/w to 90% w/w, more preferably 30% w/w to 90% w/w, even more preferably 30% w/w to 60% w/w and most preferably 30% w/w to 40% w/w.

In a further preferred embodiment of the invention, instead of $H_2O_2$ a derivative capable of generating $H_2O_2$ as a sterilization agent during sterilization conditions is used. Examples of such derivatives are peracids, carbamide peroxides, triphenylphosphine oxide and acetone peroxide.

In a further embodiment of the invention, the sterilization agent comprises $H_2O_2$ or a derivative thereof, capable of generating $H_2O_2$ as the sterilising component under sterilization conditions, or a mixture of two or more thereof, as the only sterilising component.

In another embodiment the sterilzation agent comprising $H_2O_2$ or a derivative thereof, capable of generating $H_2O_2$ as the sterilising component under sterilization conditions is used in combination with other sterilization means or agents, e.g. one or more of heat, UV or gamma radiation, or chemical or biological sterilization components, in particular ozone.

Sterilization conditions in the sense of the invention is an environment with a defined pressure, humidity and temperature, in which sterilization takes place. The respective conditions are known in the art.

Objects in the sense of the invention are particularly medical objects. Especially with medical devices, it is important that a good hemocompatibility is assured, since they are likely to come into contact with the blood circulation of a patient.

In one embodiment, the objects are those that are used in hemodialysis, particularly blood piping elements, such as tubes, tubing systems or filters, or elements coming into contact with blood, such as apparatuses in slaughterhouses or in the blood processing industry. Nevertheless, the term objects is not limited to the above objects but comprises all objects that might come into contact with blood, such as surgical instruments in general or stents.

Medical objects according to the invention are particularly tubes and tubing systems for medical apparatuses, components of a cardiovascular systems, components of blood transfusion systems or components of chirurgical systems, such as artificial organs or means for blood embolization.

In a further preferred embodiment of the invention, the object is a medical object useful in hemodialysis.

Medical objects useful in hemodialysis according to the invention are particularly components of dialyzers, such as tubes, tubing systems, filters, deaerators, drip chambers, pump tubes for the peristalsis or centrifuges.

In hemodialysis, particularly in single-needle-systems where the blood stays a relatively long time outside of the body, it is vital that the blood does not coagulate in the components of the dialyzer. Nor should the blood-cells be destroyed since the blood is reinjected in the patient after having been cleaned.

In a further embodiment of the invention, the object is a tube system.

The preparation of the tubes for the contact with blood is particularly advantageous, since a major portion of the extracorporeal blood circulation consists of tubes. This means that transported blood is in contact with the tubes for a long time. Therefore, the hemocompatibility of the tubes has a significant impact on the hemocompatibility of a medical device including an extracorporeal blood circulation.

Hemocompatibility is the compatibility of objects with blood. The hemocompatibility of objects is given when these objects allow contact with flowing blood of a human or an animal without causing adverse reactions such as thrombosis, hemolysis, complement activation or inflammation, or at least when such reactions are minimized to a significant extent.

Enhancing the hemocompatibiliy in the sense of the invention means improving at least one parameter defined in the International Standard ISO 10993 Part 4 "Biological evaluation of medical devices—Selection of tests for interactions with blood".

In one embodiment, the enhancement of hemocompatibility is determined compared to an object, which has not been sterilized with a $H_2O_2$ containing sterilization agent, e.g. an object that was sterilized with e-beam, gamma radiation and/or ozone, respectively, i.e. without the use of a $H_2O_2$ containing sterilization agent.

By the use of a $H_2O_2$ containing sterilization agent, the activation of the coagulation is reduced, shown by a lower thrombin-antithrombin III-complex (TAT-complex), indicating the activation of thrombin, the central enzyme of the coagulation cascade, the loss of the number of platelets caused by adhesion at the object surface or by platelet aggregation is reduced, the activation of the complement system acting as a defence mechanism against immigrated microorganisms is reduced and/or the haemoglobin release occurring during damage of red blood cells which is called hemolysis is reduced.

Thus, the use of a $H_2O_2$ containing sterilization agent reduces the level of coagulation activation and/or reduces the loss of platelets and/or results in a lower concentration of anaphylatoxin C5a and/or reduces the hemolysis during the contact of the object with blood, e.g. during medicinal use of the object.

In a further embodiment of the invention, the object is a single-needle-system and the sterlization agent comprises $H_2O_2$ as the only sterilizing component. In a further embodiment of the invention, the object is a single-needle-system and the sterlization agent comprises $H_2O_2$ as the only sterilizing component and a reduction of the level of coagulation activation and/or a reduction of loss of platelets and/or a lowering in the concentration of anaphylatoxin C5a and/or a reduction of hemolysis during the contact of the object with blood, e.g. during medicinal use of the object is achieved.

In a further embodiment of the invention, the object is a tube or a tubing system and the sterlization agent comprises $H_2O_2$ as the only sterilizing component.

In a further embodiment of the invention, the object is a tube or a tubing system and the sterlization agent comprises $H_2O_2$ as the only sterilizing component and a reduction of the level of coagulation activation and/or a reduction of loss of platelets and/or a lowering in the concentration of anaphylatoxin C5a and/or a reduction of hemolysis during the contact of the object with blood, e.g. during medicinal use of the object is achieved.

Thus, the hemocompatibility of the objects sterilized by the use of $H_2O_2$ according to the invention is significantly enhanced.

Further details and advantages will now be explained in more detail by way of examples and with reference to the figures.

EXAMPLES

The experimental procedure of the examples was as follows:

The experimental procedure was developed in compliance with the International Standard ISO 10993 Part 4 "Biological evaluation of medical devices—Selection of test for interactions with blood".

The test items, PVC tubes of a dialyzer system, were fixed on a board. The test systems consisted of tubes as bloodlines forming, together with a blood pump, a recirculation system for blood. In each experiment of both examples, two test systems (test vs. reference item) were evaluated in parallel in a standard incubator (Memmert, Schwabach, Germany). The temperature was set to 37° C. in all experiments. This test was effectuated three times with the whole blood of three different donors representing the tests A, B and C with the test items and representing the tests R1, R2 and R3 with the respective reference items in FIGS. 1 to 8.

The test items were preconditioned for 3 hours up to 60° C. in an external heating cabinet. Then they were sterilized with vapor of a 36% w/w $H_2O_2$ concentration in a full cycle sterilization (24 cycles in total). After that, the test items were stored in a clima cabinet at 15° C. and 65% r.h.

The reference items were sterilized by e-beam sterilization. These were also stored in a clima cabinet at 15° C. and 65% r.h.

The experimental procedure was conducted 11 to 18 days after the sterilization of the items.

For the experimental procedure, blood was drawn from healthy volunteers, denying any medication with known influence on the platelets or coagulation. 450 ml whole blood was collected using a 17 G (1.5 mm) fistula needle. In the blood bag 750 IU heparin diluted in 50 ml saline solution results in a concentration of 1.5 IU/ml in the final mixture of blood and saline (9:1). Within 30 minutes after blood collection, the hemocompatibility experiments started.

In the experimental procedure, the test systems were firstly prerinsed with a saline solution (0.9% NaCl) for approximately 30 min. To simulate dialysis treatment, the systems were filled with 190 ml whole blood and blood flow was adjusted to 250 ml/min. Sampling times were at 15, 30, 60, 120 and 180 minutes. Before filling samples were taken out of the blood bag as "pre"-values. As "post"-values, samples were taken out of a separately stored syringe.

The evaluation parameter chosen for the laboratory analysis, thrombin-antithrombin III-complex, blood cells, complement factor 5a, free hemoglobin) reflect blood response concerning coagulation activation, blood cell adhesion, immune response and damage of red blood cells. The used methods, test kits and standard operation procedures are as follows:

| Parameter | Method | Manufacturer |
|---|---|---|
| Thrombin-antithrombin III-complex (TAT) | ELISA, Enzygnost TAT micro | Dade Behring (Marburg, Germany) |
| Platelets (PLT), leucocytes (WBC), erythrocytes (RBC), hematocrit (HTC), total hemoglobin (HGB) | K4500, cell counter | Sysmex (Norderstedt, Germany) |
| Complement factor 5a | ELISA, EIA-3327 | DRG (Marburg, Germany) |
| Free hemoglobin (fHb) | Cripps | — |

In order to be able to compare all single results of a test, special indices were defined. "Mean TAT increase per hour", "Mean platelet loss", "Mean C5a decrease per hour" and "Normalized index of hemolysis" were used to simplify evaluation of the test results.

In the first example, the reference and test items were tubing systems of a double-needle-dialyzing system "AV-Set Online plus 5008" of Fresenius Medical Care. The tubes of this system consist of PVC.

Figure 1:
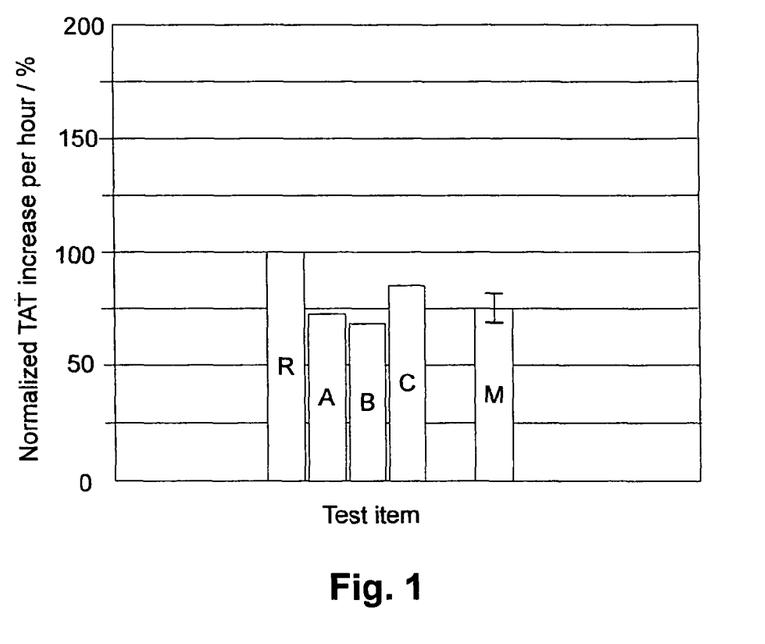
FIG. 1 is a diagram representing the normalized mean TAT increase per hour of a blood probe of a first example.

FIG. 1 refers to the thrombin-antithrombin III-complex (TAT) of the sample blood of the test and the reference item after the experimental procedure of the first example. Thrombin, the central enzyme of the coagulation cascade, is inactivated by antithrombin III forming the TAT complex. Increase TAT concentrations indicate the activation of the blood coagulation.

As can be seen from FIG. 1, coagulation activation was found at a lower level for the test item (A, B, C) with respect to the respective reference item (R=100%) (Mean M: 74±11%; VK (variation coefficient)=15%; test A: 71%; test B: 65%; test C: 86%).

Figure 2:
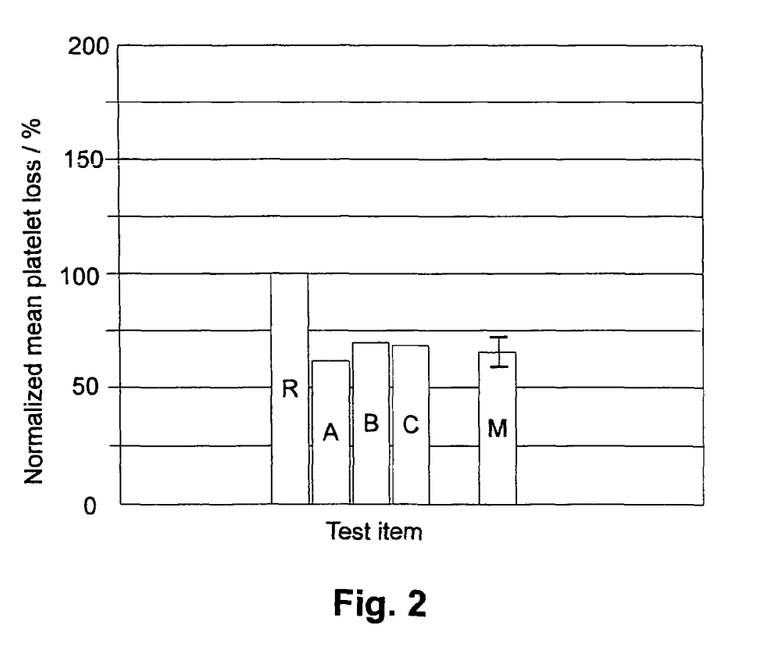
FIG. 2 is a diagram representing the normalized mean platelet loss of a blood probe of the first example.

FIG. 2 refers to platelet loss of the sample blood of the test and the reference item after the experimental procedure of the first example. Platelet loss is caused by adhesion at the surface of the material or by platelet aggregation.

As can be seen from FIG. 2, platelet loss was lower for the test items (A, B, C) with respect to the respective reference items (R=100%) (Mean M: 65±5%; VK=8%; test A: 59%; test B: 69%; test C: 67%).

Figure 3:
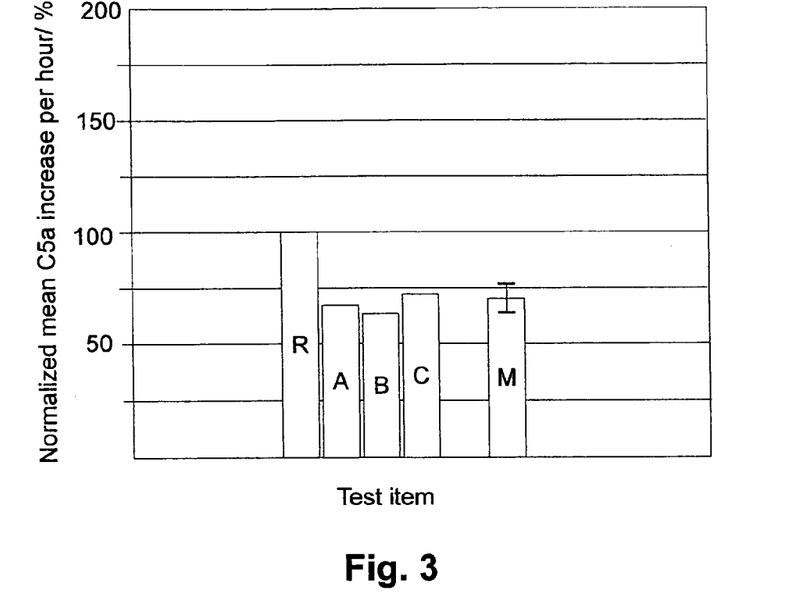
FIG. 3 is a diagram representing the normalized mean C5a increase per hour of a blood probe of the first example.

FIG. 3 refers to the complement factor 5a of the sample blood of the test and the reference item after the experimental procedure of the first example. The complement system acts as a defense mechanism against immigrated microorganisms. Its activation sets the anaphylatoxin C5a free and leads to increased concentrations of C5a.

As can be seen from FIG. 3, complement activation showed a clear donor dependence. Nevertheless, the normalized values were lower for the test items (A, B, C) with respect to the respective reference items (R=100%) (Mean M: 66±4%; VK=7%; test A: 65%; test B: 62%; test C: 71%).

Figure 4:
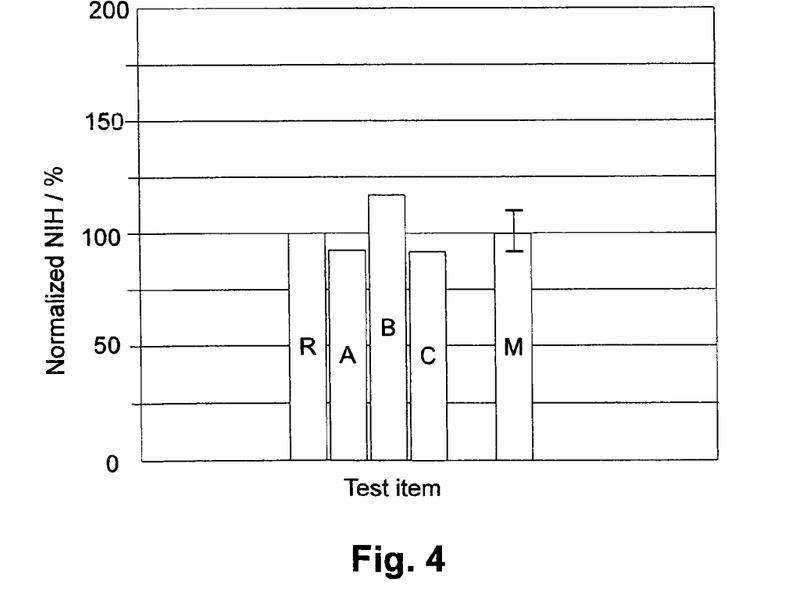
FIG. 4 is a diagram representing the normalized index of hemolysis (NIH) of a blood probe of the first example.

FIG. 4 refers to the free hemoglobin of the test and the reference item after the experimental procedure of the first example. Hemoglobin release occurs during damage of red blood cells which is called hemolysis. An increased concentration of free hemoglobin indicates hemolysis.

As can be seen from FIG. 4, wherein the normalized index of hemolysis is shown, hemolysis was the same for the test items (A, B, C) with respect to the respective reference items (R=100%) (Mean M: 99±16%; VK=16%; test A: 90%; test B: 117%; test C: 90%).

In the second example, the reference and test items were tubing systems of a single-needle-dialyzing system "SN-Set Online plus 5008" of Fresenius Medical Care. The tubes of this system consist of PVC.

Figure 5:
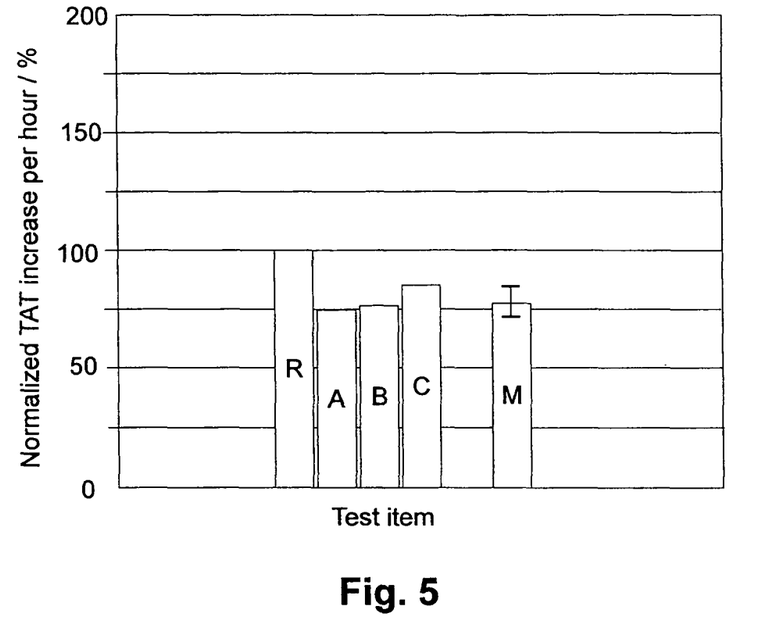
FIG. 5 is a diagram representing the normalized mean TAT increase per hour of a blood probe of a second example.

FIG. 5 refers to the thrombin-antithrombin III-complex (TAT) of the sample blood of the test and the reference item after the experimental procedure of the second example.

As can be seen from FIG. 5, coagulation activation was found at a lower level for the test items (A, B, C) with respect to the respective reference items (R=100%) (Mean M: 78±6%; VK=7%; test A: 74%; test B: 76%; test C: 85%).

Figure 6:
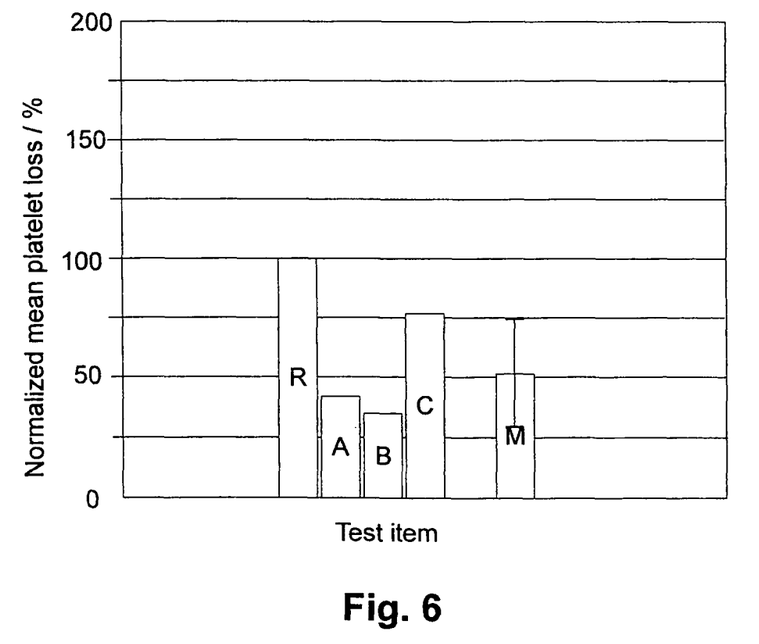
FIG. 6 is a diagram representing the normalized mean platelet loss of a blood probe of the second example.

FIG. 6 refers to platelet loss of the sample blood of the test and the reference item after the experimental procedure of the second example.

As can be seen from FIG. 6, platelet loss was lower for the test items (A, B, C) with respect to the respective reference items (R=100%) (Mean M: 51±23%; VK=45%; test A: 43%; test B: 34%; test C: 77%).

Figure 7:
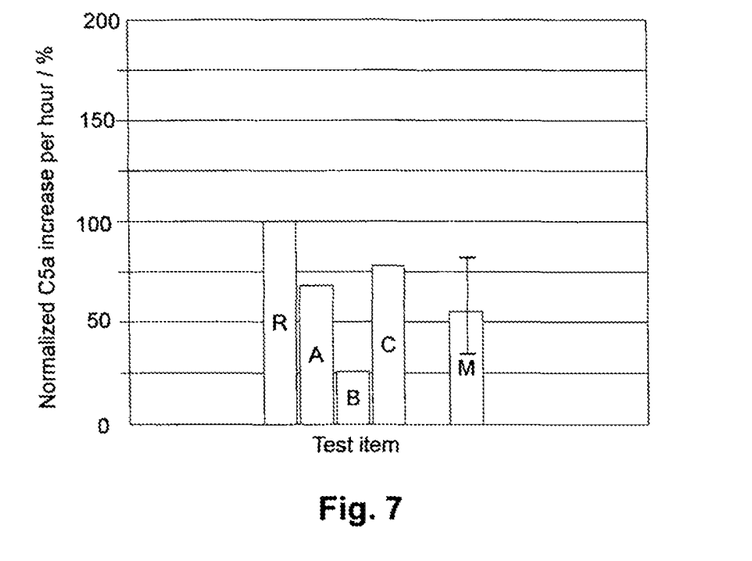
FIG. 7 is a diagram representing the normalized mean C5a increase per hour of the second example.

FIG. 7 refers to the complement factor 5a of the sample blood of the test and the reference item after the experimental procedure of the second example.

As can be seen from FIG. 7, complement activation showed a clear donor dependence. Nevertheless, the normalized values were lower for the test items (A, B, C) with respect to the respective reference items (R=100%) (Mean M: 58±27%; VK=47%; test A: 70%; test B: 27%; test C: 77%).

Figure 8:
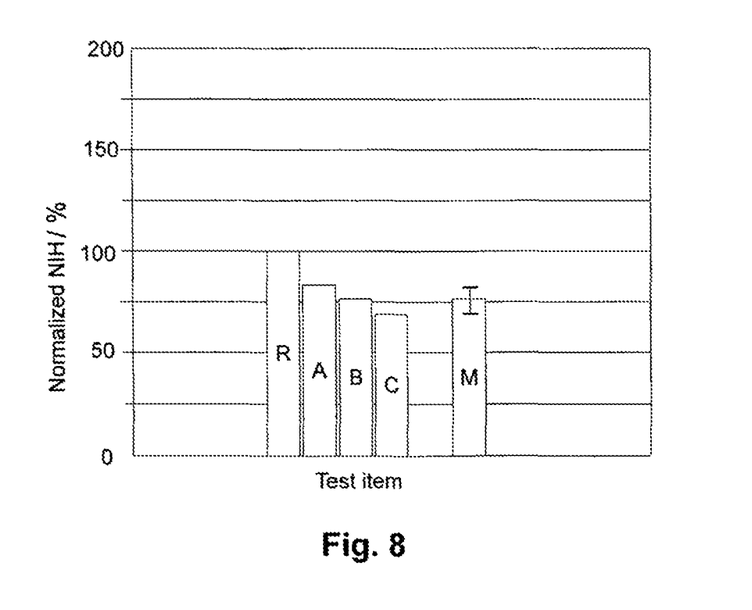
FIG. 8 is a diagram representing the normalized index of hemolysis (NIH) of a blood probe of the second example.

FIG. 8 refers to the free hemoglobin of the test and the reference item after the experimental procedure of the second example.

As can be seen from FIG. 8, wherein the normalized index of hemolysis is shown, hemolysis was lower for the test items (A, B, C) with respect to the respective reference items (R=100%) (Mean M: 76±9%; VK=11%; test A: 85%; test B: 76%; test C: 68%).

To conclude, for the first and the second example, all parameters considered for hemocompatibility showed an amelioration or at least did not degrade for the test items sterilized with a $H_2O_2$ concentration in comparison to the test items sterilized with e-beam. Therefore, the hemocompatibility of the test item was better for coagulation activation, platelet loss, complement activation and hemolysis.

Figure 9:
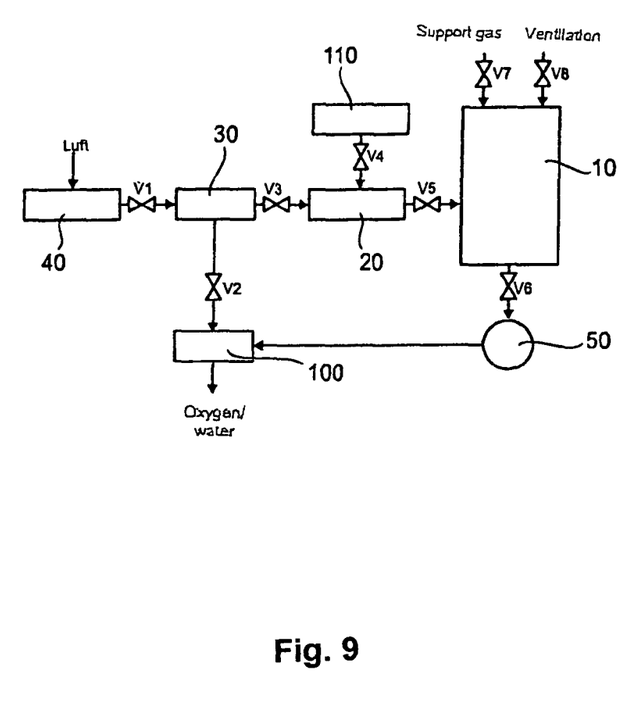
FIG. 9 is a schematic representation of a preferred sterilization apparatus in accordance with the present invention.

The sterilization of the invention and in particular the experimental procedures of the above described examples can be implemented by the sterilization apparatus and/or method described in the following:

FIG. 9 shows a block diagram for an embodiment of a sterilization apparatus in accordance with the present invention. A sterilization chamber is labeled by the reference numeral 10 which can, for example, have a volume of at least 1 m³ and a door which serves both loading and unloading. The objects to be sterilized can be introduced into the sterilization chamber 10, for example, on steel baskets on one or more levels. 150 to 200 products can be sterilized simultaneously depending an the product size. An aerospace container 20 or a vaporizer 20 is connected before the sterilization chamber 10.

As can furthermore be seen from FIG. 9, an oxygen generator 40 is connected before the ozone generator 30 and 95% oxygen can be acquired from the environmental air in it. A molecular screen or zeolite serves this purpose, for example. The oxygen is converted into ozone in the ozone generator 30, which can take place, for example, by a dielectric barrier discharge.

If the method in accordance with the invention is only carried out with $H_2O_2$, the Figure shown in FIG. 9 can be made correspondingly modified. For example, the ozone generator 30 can then be dispensed with. Instead, for example, a reservoir or a tank can be provided for the $H_2O_2$ or generally a $H_2O_2$ supply can be provided. The $H_2O_2$ is preferably introduced into the sterilization chamber 10 in steam form, for instance as liquid vaporized by evacuation.

A catalytic converter is labelled by the reference numeral 100 in FIG. 9 which is suitable to decompose the sterilization agent after its use, in particular to decompose $H_2O_2$ and/or ozone or their reaction products. Only water and oxygen are then created as decomposition products. The catalyst 100 can, for example, be manganese dioxide.

To generate the desired vacuum in the sterilization chamber 10, a vacuum pump 50 is connected after said sterilization chamber which results in an evacuation of the sterilization chamber 10 with an opened valve V6 and with a vacuum pump 50 in operation. Sterile air is introduced as a support gas into the sterilization chamber 10 via the valve V7. Finally, a unit is indicated by the reference numeral 110 which serves the metering in of water and/or $H_2O_2$ into the aerosol container 20 or to the vaporizer 20.

The sterilization procedure has the following form in detail:

After the insertion of the object or objects into the sterilization chamber 10, a vacuum is generated in the sterilization chamber 10, for which purpose only the valve V6 in accordance with FIG. 9 is opened and all the further valves V1, V2, V3, V4, possibly V5, V7 and V8, are closed. The generation of the vacuum results in a reduction of the chamber pressure.

The pressure in the chamber 10 preferably drops to a value <10 mbar in step 200 due to the evacuation of the sterilization chamber 10 by means of the vacuum pump 200.

For the humidification, the valve V5 in the line between the aerosol container 20 or the vaporizer 20 and the sterilization chamber 10 can e.g. be opened so that a vaporization of the liquid in the aerosol container 20 takes place, provided its vapor pressure is fallen below. If the vapor pressure of the liquid, i.e. for example of the mixture of water and $H_2O_2$, is fallen below in the aerosol container, it starts to vaporize and in this manner enters into the sterilization chamber 10. The vacuum pump 50 is thus not used only for evacuating, but also for vaporizing the liquid in the aerosol container 20.

A sterilization agent is actively introduced into the sterilization chamber 10 simultaneously with the step of humidifying. This method step is labeled by the reference numeral 201 in FIG. 10. $H_2O_2$ is advantageously introduced as the sterilization agent into the sterilization chamber as vapor here, for example.

Alternatively, the creation of hydroxide radicals can take place due to the contact of the ozone with water and/or $H_2O_2$, said hydroxide radicals entering into the sterilization chamber 10 with the aerosol and there contributing to the sterilization process or representing the decisive sterilization agent.

Figure 11:
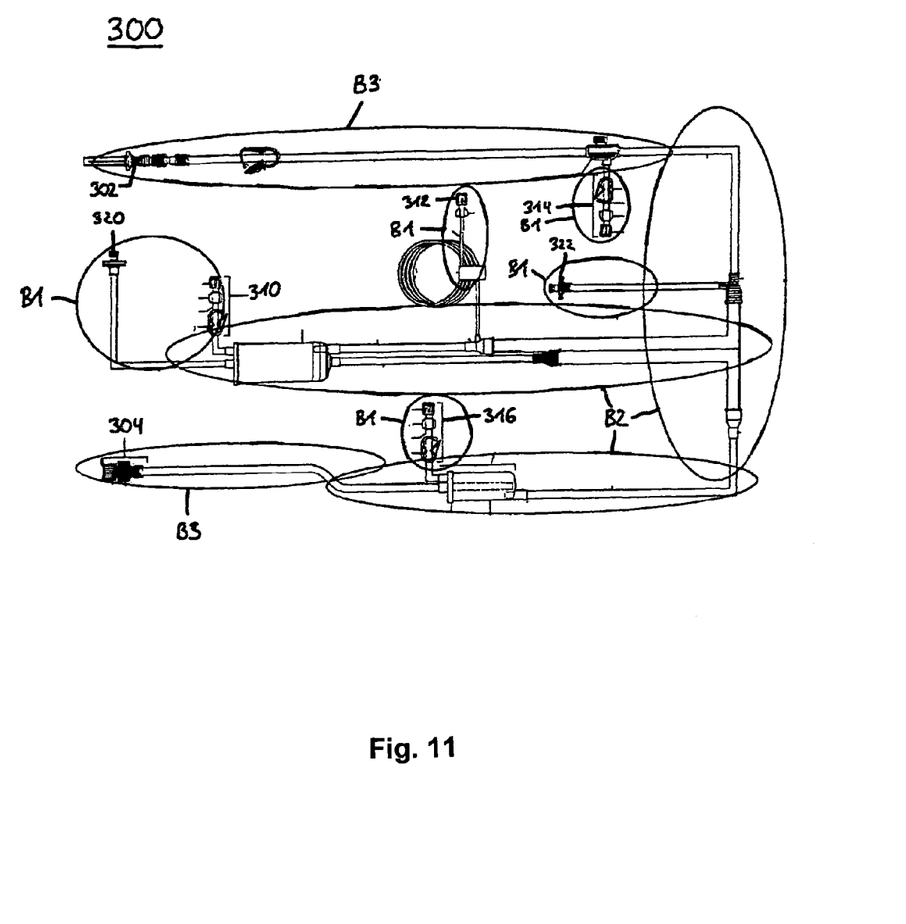
FIG. 11 is a schematic representation of a medical tubing system with indication of different sterilization regions.

The valves V3 and V5 or V4 and V5 are opened and all the further valves are closed during the method step 201 in accordance with FIG. 11. The aerosol containing ozone enters into the sterilization chamber 10 due to the pressure drop between the ozone generator 30 and the sterilization chamber 10.

This applies correspondingly to the $H_2O_2$ vapor when $H_2O_2$ is used as the sterilization agent instead of ozone.

Figure 10:
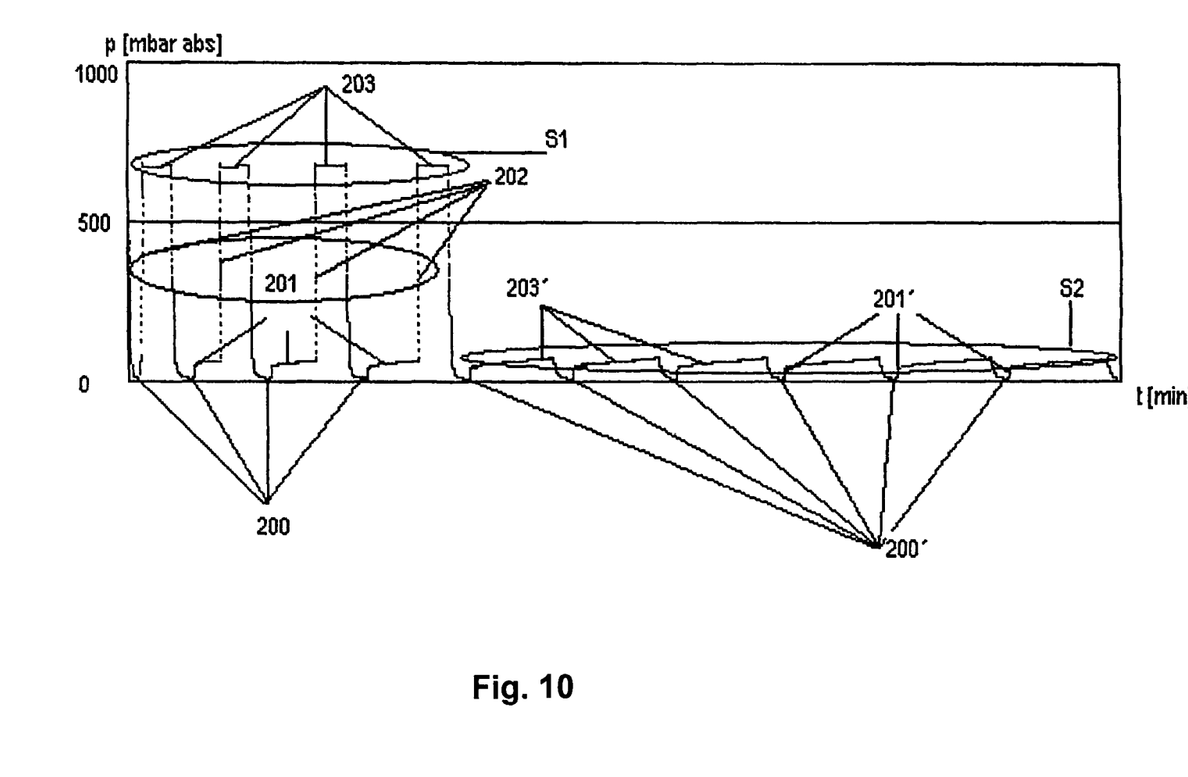
FIG. 10 is a representation of a preferred pressure profile in the sterilization chamber during a preferred sterilization cycle.

A pressure increase thereby occurs such as can be seen from FIG. 10. This pressure increase is a measure for the quantity of the sterilization agent in the sterilization chamber 10. In this respect, the concentration is set to a value ideal for the product to be sterilized.

After the introduction of the sterilization agent, the pressure in the sterilization chamber 10 is increased by means of a support gas via the valve V7, as is shown in step 202 in accordance with FIG. 10. In the embodiment shown there, the pressure is increased to a first support pressure of approximately 500 mbar abs. This support gas enters into the sterilization chamber 10 in that the valve 7 in accordance with FIG. 9 is opened for a predetermined duration or until a specific pressure value is reached. All the further valves of the apparatus are closed during this method step. V5 can alternatively also be open. The sterilization phase in which the first pressure gas is applied is called the first sterilization phase S1.

As can further be seen from FIG. 10, the first support pressure is held in the sterilization chamber 10 for a specific duration. This method step is identified by the reference numeral 203 in FIG. 10 and can be, for example, a minute or in the minute region.

After the holding of the support pressure for a specific duration in accordance with step 203 in FIG. 10, this process step comprising the steps 200 to 203 are carried out four times in total, i.e. it is evacuated, then humidified and the sterilization agent is introduced and then the first support pressure is again generated and held for a specific duration.

After the fourfold carrying out of the steps 200 to 203, the first sterilization phase S1 is terminated and the process continues with the second sterilization phase S2. In the sterilization phase S2, the second support pressure is applied which here amounts to 50 mbar abs and the steps 200', 201', 202' and 203' are carried out a total of six times. In this respect, steps 200' to 203' correspond to steps 200 to 203 from the sterilization phase S1, i.e. it is evacuated, then humidified and the sterilization agent is introduced and then the second support pressure is generated again, with the difference that the second support pressure in the sterilization phase S2 amounts to 50 mbar abs.

Due to the fact that the filling of the sterilization chamber 10 with sterilizing agent in accordance with step 201, 201', 201" is terminated when a substantial underpressure is present in the sterilization chamber 10, it can generally be achieved that an underpressure is always present in the aerosol generator 20. This makes it possible that liquid, i.e. water, $H_2O_2$ and/or a mixture of both substances, can subsequently easily be drawn from a reservoir 110 by opening the valve V4.

As can furthermore be seen from FIG. 9, the pump 50 is in communication at the outlet side with the catalyst 100 so that the medium arising at the pressure side of the pump can be decomposed in the catalyst 100.

It is generally conceivable to repeat and/or to vary the sterilization phases S1 and S2, for example, or to carry out further sterilization phases at different support pressures subsequently to the sterilization phases shown in FIG. 10.

This is followed in the embodiment shown here by the flushing and degassing of the sterilization chamber 10 by multiple evacuation and ventilation. This phase is not shown in any more detail in FIG. 10.

An evacuation and a ventilation of the sterilization chamber 10 takes place multiple times during the flushing and degassing phase. This phase can be followed by a drying phase in which there is preferably a vacuum in the sterilization chamber 10.

FIG. 11 shows a tube system 300 or a so-called tubing system 300 which was sterilized by means of the apparatus and method shown in FIGS. 9 and 10. It is a tubing system 300 for dialysis which can have a total tube length of up to 6 m in dependence o the treatment process.

The packing for the tubing system 300 in which the tubing system 300 is, however, preferably sterilized is not shown. It is conceivable that at least one support pressure above the atmospheric pressure is applied or is being applied in such a case.

The tubing system 300 in accordance with FIG. 11 is a tubing system 300 for the extracorporeal blood circuit which in particular has a needle 302 for connection of the tubing system 300, e.g. to the shunt of the patient, a connector 304 e.g. for connection to the dialyzer, not shown, inflows and outflows 310, 312, 314, 316 closed by closure caps and pressure measurement connections 320, 322.

The regions labeled with B1 are sterilized by the application of the first support pressure of approximately 500 mbar abs, that is, during the sterilization phase S1 shown in more detail in FIG. 2. All the regions of the tubing system 300 in which the lumen of the tubing system 300 is closed at the end side are affected, that is, the inflows or outflows 310, 312, 314, 316 closed by closure caps and the pressure measurement connections 320, 322. It is conceivable that with particularly long tubing systems 300, the middle region of the tubing system 300 is likewise sterilized during the sterilization phase S1.

The regions labeled by B2 are likewise sterilized by the application of the first support pressure of approximately 500 mbar abs. All the regions of the tubing system 300 which are in the inner region of the lumen of the tubing system 300 are affected so that the first support pressure 300 is necessary or sufficient to transport the sterilization agent in it.

The regions labeled with B3 are sterilized by the application of the second support pressure or gassing pressure of approximately 50 mbar abs, that is, during the sterilization phase S2 shown in more detail in FIG. 10. These regions in FIG. 3 are here the start regions and end regions of the tubing system 300, that is, the regions which follow the needle 302 and the connection 304 respectively.

The above described sterilization method and apparatus include the following embodiments: A method for sterilizing at least one object 300, wherein the object 300 is exposed to a sterilization agent, wherein at least one first support pressure and at least one second support pressure are applied and wherein a sterilization of at least one first region B1 of the object 300 takes place by the sterilization agent at the first support pressure and a sterilization of at least one second region B2 of the object 300 takes place at the second support pressure. A method wherein the sterilization agent at least partly includes ozone and/or hydrogen peroxide or one or more of the reaction products of these substances. A method wherein the at least one first support pressure and/or the at least one second support pressure is/are generated by introducing a support gas into a sterilization chamber 10. A method wherein the support gas includes at least partially an inert gas and/or air, preferably includes or is sterile air. A method wherein in a first step, the object 300 to be sterilized is inserted into a sterilization chamber 10, in a second step 200, the sterilization chamber 10 is evacuated; and, in a third step 201, the sterilization chamber 10 is humidified and sterilization agent is introduced into the sterilization chamber 10; in a fourth step 202, the first support pressure is applied; in a fifth step 203, the first support pressure is maintained for a point in time or for a duration; in a sixth step, steps two to five are repeated once or a multiple of times; and in a seventh step, the at least one second support pressure is applied. A method, wherein in the seventh step, steps two to five or two to six are carried out at the second support pressure. A method, wherein in at least one further step, one or more further support pressures are applied; and in that steps two to five or two to six are accordingly carried out at the further support pressures. A method wherein the humidification of the sterilization chamber 10 takes place in that a liquid, in particular a mixture containing water and hydrogen peroxide, is brought to vaporization by application of a vacuum, in particular by the evacuation, and the vaporized liquid is supplied to the sterilization chamber 10. A method, wherein the first support pressure is at least approximately 500 mbar abs and/or the second support pressure is at least approximately 50 mbar abs. A method wherein a third support pressure is applied, wherein the third support pressure is preferably up to approximately 50 mbar abs and/or corresponds to the gassing pressure without additional introduction of a support gas, with the fourth step already being carried out by step three. A method, wherein the sterilization agent is introduced into the sterilization chamber 10 in the form of an aerosol. A method, wherein the aerosol is formed by vapor containing hydrogen peroxide; and/or in that the aerosol is created by introduction of ozone into a liquid which contains water and/or hydrogen peroxide. A method, wherein the introduction of a sterilization agent into the sterilization chamber 10 takes place at a pressure in the sterilization chamber 10 which is below the atmospheric pressure. A method, wherein the holding of the support pressure, preferably in accordance with the fifth step 203 takes place for a duration whose length is in the range <20 minutes, preferably <10 minutes and particularly preferably <5 minutes. A method, wherein the duration between two application steps taking place successively, preferably in accordance with the fourth step 202 is in the range <20 minutes, preferably <15 minutes, and particularly preferably <10 minutes. A method, wherein after the last method step, in particular after the seventh step or after termination of the sterilization, the flushing and degassing of the sterilization chamber 10 is carried out, with the flushing and degassing preferably being carried out a multiple of times. A method, wherein the sequence of the steps two to five lasts approximately 15 to 20 minutes, preferably approximately 18 minutes.

A sterilization apparatus having at least one sterilization chamber 10 for the reception of at least one object 300 to be sterilized, having at least one first means for the supply and/or removal of a sterilization agent, having at least one second means by means of which at least one first support pressure and at least one second support pressure can be applied, and wherein at the first support pressure of the sterilization agent a sterilization of a first region B1 of the object 300 can be carried out and at a second support pressure a sterilization of a second region B2 of the object 300 can be carried out. A sterilization apparatus, wherein the sterilization apparatus has at least one control and/or regulation means by means of which the sterilization procedure can be controlled and/or regulated and/or monitored, can preferably be semiautomatically and/or fully automatically controlled and/or regulated and/or monitored. A sterilization, wherein a method in accordance with one of the above described methods can be carried out using the sterilization apparatus.

The invention claimed is:

1. A method comprising:
using a sterilization agent comprising $H_2O_2$ or a derivative thereof, capable of generating $H_2O_2$ as the sterilising component under sterilization conditions, for enhancing the hemocompatibility of objects;
wherein the sterilization agent is used in combination with agents comprising heat, UV or gamma radiation, ozone, or combinations thereof.

2. The method according to claim 1, wherein the object is a medical object, in particular an object that may be in contact with blood during use.

3. The method according to claim 2, wherein the object is a medical object useful in hemodialysis.

4. The method according to claim 1, wherein the object is a tubing system.

5. The method according to claim 1, wherein $H_2O_2$ under sterilization conditions has a concentration of 3% w/w to 90% w/w.

6. The method according to claim 1, wherein said derivative is selected among peracids, carbamide peroxides, triphenylphosphine oxide and acetone peroxide.

7. The method according to claim 1, wherein the enhanced hemocompatibility comprises at least one of the following characteristics: reduction of the level of coagulation activation, a reduction of the loss of platelets, a lower concentration of anaphylatoxin C5a, and a decrease in hemolysis during use of the object.

8. The method according to claim 1, wherein the enhancement of hemocompatibility, the reduction of the level of coagulation activation, the reduction of the loss of platelets, the lower concentration of anaphylatoxin C5a, and the decrease in hemolysis during use of said object are respectively achieved compared to an object that has been sterilized with a sterilization agent not containing $H_2O_2$.

9. The method according to claim 1, wherein $H_2O_2$ under sterilization conditions has a concentration of 10% w/w to 90% w/w.

10. The method according to claim 1, wherein $H_2O_2$ under sterilization conditions has a concentration of 30% w/w to 90% w/w.

11. The method according to claim 1, wherein $H_2O_2$ under sterilization conditions has a concentration of 30% w/w to 60% w/w.

12. The method according to claim 1, wherein $H_2O_2$ under sterilization conditions has a concentration of 30% w/w to 40% w/w.

13. A method comprising:
using a sterilization agent comprising $H_2O_2$ or a derivative thereof, capable of generating $H_2O_2$ as the sterilising component under sterilization conditions for achieving at least one of the following characteristics within an object: reduction of the level of coagulation activation, a reduction of the loss of platelets, a lower concentration of anaphylatoxin C5a, and a decrease in hemolysis during use of said object;
wherein the sterilization agent is used in combination with agents comprising heat, UV or gamma radiation, ozone, or combinations thereof.

* * * * *